(12) United States Patent
Kagemann, Jr. et al.

(10) Patent No.: US 10,575,723 B2
(45) Date of Patent: Mar. 3, 2020

(54) MAPPING OF INTERNAL FEATURES ON EN FACE IMAGERY

(71) Applicants: University of Pittsburgh—Of the Commonwealth System of Higher Education, Pittsburgh, PA (US); The Regents of the University of Michigan, Ann Arbor, MI (US)

(72) Inventors: Lawrence E. Kagemann, Jr., Pittsburgh, PA (US); Joel Steven Schuman, Pittsburgh, PA (US); Sayoko Eileen Moroi, Ann Arbor, MI (US)

(73) Assignees: University of Pittsburgh—Of the Commonwealth System of Higher Education, Pittsburgh, PA (US); The Regents of the University of Michigan, Ann Arbor, MI (US)

( * ) Notice: Subject to any disclaimer, the term of this patent is extended or adjusted under 35 U.S.C. 154(b) by 264 days.

(21) Appl. No.: 15/550,021

(22) PCT Filed: Feb. 24, 2016

(86) PCT No.: PCT/US2016/019253
§ 371 (c)(1),
(2) Date: Aug. 9, 2017

(87) PCT Pub. No.: WO2016/138076
PCT Pub. Date: Sep. 1, 2016

(65) Prior Publication Data
US 2018/0235457 A1 Aug. 23, 2018

Related U.S. Application Data

(60) Provisional application No. 62/120,636, filed on Feb. 25, 2015, provisional application No. 62/209,543, filed on Aug. 25, 2015.

(51) Int. Cl.
*A61B 3/00* (2006.01)
*A61F 9/007* (2006.01)
(Continued)

(52) U.S. Cl.
CPC ............ *A61B 3/0025* (2013.01); *A61B 3/102* (2013.01); *A61B 3/1241* (2013.01); *A61B 3/14* (2013.01);
(Continued)

(58) Field of Classification Search
CPC ......... G06T 7/0012; G06T 2207/10101; G06T 2207/30041; A61B 3/0025; A61B 3/102;
(Continued)

(56) References Cited

U.S. PATENT DOCUMENTS 8,223,143 B2   7/2012  Dastmalchi et al. ......... 345/418
10,022,065 B2 * 7/2018  Ben-Yishai et al. ... A61B 5/055
(Continued)

FOREIGN PATENT DOCUMENTS

WO   WO 2014/121268 A1   8/2017 ............. A61F 9/007

OTHER PUBLICATIONS

International Preliminary Report on Patentability issued in related International Patent Application No. PCT/US 2016/019253, dated Sep. 8, 2017.
(Continued)

*Primary Examiner* — Andrew W Johns
(74) *Attorney, Agent, or Firm* — Foley & Lardner LLP (57) ABSTRACT

The present disclosure describes systems and method for generating surgical maps that provide a surgeon with information regarding the placement of features of interest. More particularly, the system is configured to display optical coherence tomography (OCT) images to a medical professional. The medical professional can select anatomical features, biomarkers, and other features of interest within each
(Continued)

of the OCT images. The system can then translate the location of the features of interest within the OCT images to an en face image to generate a map of the features that the medical professional can use for surgical guidance.

20 Claims, 7 Drawing Sheets

(51) Int. Cl.
    *A61B 3/14*         (2006.01)
    *A61B 3/10*         (2006.01)
    *A61B 3/12*         (2006.01)
    *A61B 3/16*         (2006.01)
    *A61B 34/10*       (2016.01)

(52) U.S. Cl.
    CPC ............ *A61B 3/16* (2013.01); *A61F 9/00781* (2013.01); *A61B 2034/107* (2016.02)

(58) Field of Classification Search
    CPC ................ A61B 3/1233; A61B 3/1241; A61B 2034/107
    See application file for complete search history.

(56) References Cited

U.S. PATENT DOCUMENTS

2007/0216909 A1    9/2007    Everett et al. ................ 356/479
2019/0117313 A1*  4/2019    Crawford ............... A61B 34/30

OTHER PUBLICATIONS

Sohrab, et al., "Image Registration and Multimodal Imaging of Reticular Pseudodrusen" *Investigative Ophthalmology & Visual Science*, vol. 52, No. 8, pp. 5743-5748 (2011).

Van Velthoven et al., "Overlay of conventional angiographic and en-face OCT images enhances their interpretation," *BMC Ophthalmology*, vol. 5, No. 1, pp. 1-9 (2005).

International Search Report and Written Opinion issued in related International Patent Application No. PCT/US 2016/019253, dated May 18, 2016.

* cited by examiner

MAPPING OF INTERNAL FEATURES ON EN FACE IMAGERY

CROSS-REFERENCE TO RELATED APPLICATIONS

This application is the National Phase of International Patent Application No. PCT/US2016/019,253, filed Feb. 24, 2016, which claims priority from U.S. Provisional Patent Application Nos. 62/120,636, filed Feb. 25, 2015, and 62/209,543, filed Aug. 25, 2015. The contents of these applications are incorporated herein by reference in their entirety.

GOVERNMENT SUPPORT

This invention was made with government support under EY013178 and EY008098 awarded by the National Institutes of Health. The government has certain rights in the invention.

FIELD OF THE DISCLOSURE

This disclosure generally relates to systems and methods for mapping features of interest in preparation for performing ocular surgery.

BACKGROUND

Glaucoma is the second leading cause of irreversible blindness worldwide. The primary risk factor for the diagnosis and progression of glaucoma is elevated intraocular pressure (IOP), which is created by the outflow of aqueous humor through resistance to outflow. Optical coherence tomography (OCT) images may not be able to detect constrictions in the outflow of the aqueous humor because blood within the outflow vasculature can obscure individual vessels.

Minimally or micro invasive glaucoma surgeries (MIGS) can reduce intraocular pressure (IOP) by bypassing high resistance to aqueous humor (AH) outflow in the juxtacanalicular tissue of the trabecular meshwork (TM) and inner wall of the Schlemm canal (SC). However, the outcomes of MIGS are not predictable because their success is dependent upon many complex and poorly understood factors, including a potential impediment to AH outflow in the aqueous vascular network distal to SC, which may vary from patient to patient.

MIGS are performed with little or essentially no foreknowledge of the morphology of an individual patient's aqueous humor outflow tract. To date, surgeons must review OCT cross-sectional images and attempt to memorize their general location within the patient's morphology.

Thus, there is a need in the art for improved methodologies of predicting or ascertaining the morphology of an individual patient's aqueous humor outflow tract. The present invention satisfies this need.

SUMMARY OF THE DISCLOSURE

According to one aspect of the disclosure, a surgical mapping tool is provided. The surgical mapping tool comprises (1) one or more data processors and (2) one or more storage devices. The storage devices function to store instructions that, when executed by the one or more data processors, cause the one or more data processors to retrieve image data from an optical coherence tomography device. The instructions also cause the processors to receive an indication of a location of a feature of interest within the received image data, and translate the indication of the location from a first coordinate system to a second coordinate system of an en face image. The instructions can then cause the processor to display a marker on the en face image at the location on the en face image.

In some implementations, the image data includes at least one of each of an A-scan, a B-scan, and an en face image. In some implementations, the image data includes a plurality of A-scans that are converted into a plurality of B-scans and at least one en face image.

In some implementations, the feature of interest is at least one of a Schlemm's canal, a Collector channel, a trabecular meshwork, and an outflow vessel density, a fluid flow rate, a fluid flow volume, a stiffness of a trabecular meshwork. The feature of interest can be a functional or structural feature. The indication of the location of the feature of interest identifies the feature of interest within a cross-sectional image.

In some implementations, the mapping tool is also configured to obtain a split-spectrum amplitude decorrelation algorithm (SSADA)-derived image, and then generate a third image by logically combining the SSADA-derived image date and the image data from the optical coherence tomography device. The mapping tool can combine each of the third image, the image data from the optical coherence tomography device, and the SSADA-derived image to produce a hybrid image. The feature of interest can include the hybrid image.

According to another aspect of the disclosure, a method of identifying features of interest includes receiving, by a planning tool, image data from an optical coherence tomography device. The method also includes receiving, by the planning tool, an indication of a location of a feature of interest within the received image data. The method further includes translating, by the planning tool, the indication of the location from a first coordinate system to a second coordinate system to a location on an en face image. The method also includes displaying, by the planning tool, a marker on the en face image at the location on the en face image.

In some implementations, image data includes at least one of each of an A-scan, a B-scan, and an en face image. In other implementations, the method includes generating a plurality of B-scans and at least one en face image from the plurality of A-scans. In some implementations, the feature of interest is at least one of a Schlemm's canal, a Collector channel, a trabecular meshwork, and an outflow vessel density. In some implementations, the indication of the location of the feature of interest identifies the feature of interest within a cross-sectional image.

In some implementations, the method also includes obtaining a split-spectrum amplitude decorrelation algorithm (SSADA)-derived image, and then generating a third image by logically combining the SSADA-derived image date and the image data from the optical coherence tomography device. The method can include combining each of the third image, the image data from the optical coherence tomography device, and the SSADA-derived image to produce a hybrid image. The feature of interest can include the hybrid image The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes systems and methods for generating surgical maps that provide a surgeon with information regarding the placement of features of interest. More particularly, the system is configured to display optical coherence tomography (OCT) images to a medical professional. The medical professional can select anatomical features, structural features, biomarkers, and other features of interest within each of the OCT images. The system can then translate the location of the features of interest to an en face image and overlay a feature map on the en face image that a medical professional can then use for surgical guidance.

In some implementations, the feature map enables the visualization of the aqueous humor outflow pathway. The system can employ multiple modalities to generate feature maps that include structural features. For example, the system can leverage the changing ratio of aqueous humor to blood in the outflow pathway, and by leveraging the changing ratio, the proximal and distal pathways can independently be imaged. The resulting visualizations are combined to yield an image spanning the outflow pathway from the Schlemm's canal to blood vessels, which can be used as a structural feature map.

Figure 1:
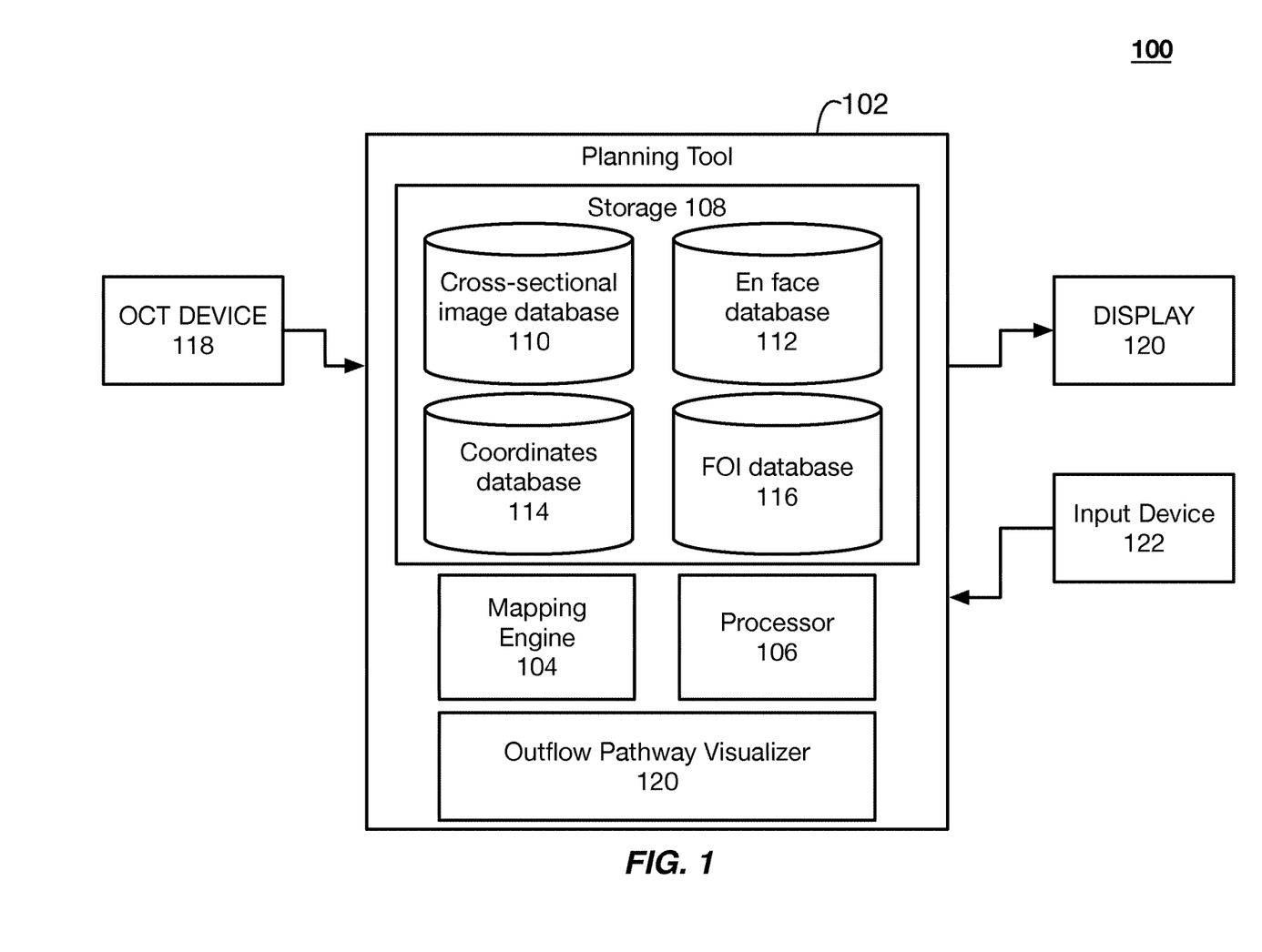
FIG. 1 illustrates a block diagram of an example system for the mapping of features of interest or biomarkers.

FIG. 1 illustrates a block diagram of an example system 100 for the mapping of features of interest, such a ocular structures and biomarkers, to generate feature maps. The system 100 includes a planning tool 102 for the mapping of anatomical and functional features of interest (FOI) onto one or more surface images (e.g., en face images). The planning tool 102 includes a mapping engine 104 and a processor 106. The planning tool 102 also includes a storage element 108, on which data and computer executable instructions can be stored. The storage element 108 can store a cross-sectional image database 110, an en face image database 112, a coordinates database 114, and/or a features of interest database 116 (also referred to as FOI database 116). The system 100 can also include an optical coherence tomography (OCT) device 118. The system 100 further includes an outflow pathway visualizer 120, which is described further in relation to FIGS. 6 and 7. The system 100 can also include a display 120 and an input device 122.

The system 100 can include one or more OCT devices 118 that generate the OCT images provided to the planning tool 102. In some implementations, the OCT device 118 is a device that can measure the retinal thickness and the retinal nerve fiber layer thickness. The OCT device 118 can be any type of OCT device that generates an OCT image. For example, the OCT device 118 can be a Cirrus HD-OCT. The Cirrus HD-OCT may generate three-dimensional (3-D) cube data of the retina, and can collect 200×200 sampling points from a 6×6 mm$^2$ area centered on the optic disc and 1024 sampling points within a 2.0 mm axial scan depth. Another example OCT device 118 can include the RTVue OCT. An RTVue OCT image may include 1019 A-scans and 768 samplings along each A-scan for a 2.3 mm axial scan depth. In some implementations, the system 100 is configured to operate with imaging devices other than OCT devices. For example, the system 100 can map features of interest using scans from other types of devices that are capable of detecting the aqueous humor outflow pathways from the surrounding tissue.

In some implementations, a number of image types can be generated from the OCT scans. For example, the OCT device 118 can generate one or more A-scans. A plurality of A-scans can be combined to create cross-sectional images, which can also be referred to as B-scan images, and en face images, which can be generated by integrating the intensity information along the axial direction of the A-scans. In some implementations, the OCT device 118 generates the A-scans, and the planning tool 102 generates the B-scans and en face images from the A-scans provided by the OCT device 118. In some implementations, the OCT device 118 is located remotely from the planning tool 102. For example, images may be captured by the OCT device 118 and then transferred to the planning tool 102 over a network.

The system 100 also includes the planning tool 102. The planning tool 102 includes one or more processors 106 that are configured to execute processor executable instructions, which may be stored in the storage element 108. The planning tool 102 also includes a mapping engine 104 configured to generate point feature maps, structural feature maps, functional feature maps, or any combination thereof. The mapping engine 104 can be an application, program, library, service, task or any type and form of executable instructions executable by the processor 106, and in general is configured to execute the methods described herein. In some implementations, the planning tool 102 is configured as an application executing on a computer. For example, the processor 106 may be the processor of the computer and the storage element 108 may be the storage of the computer or a form of remote storage. The computer may be a desktop computer, laptop computer, smart phone, tablet computer, or any other form of computing device. In some implementations, the planning tool 102 can include special purpose logic for the execution of the methods described herein. For example, the planning tool 102 can include a FPGA (field programmable gate array) or an ASIC (application specific integrated circuit).

Figures 3A, 3B:
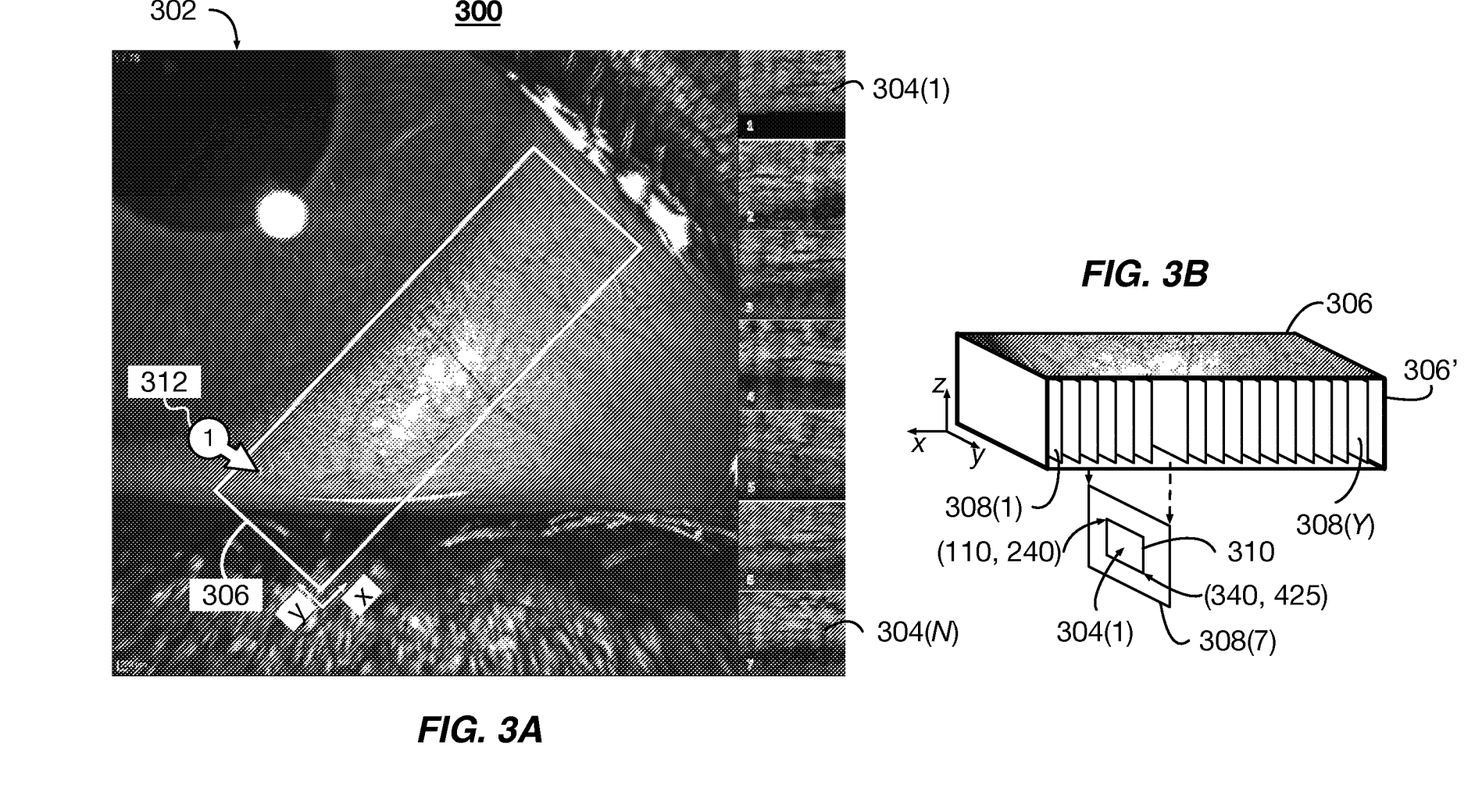
FIG. 3A illustrates an example feature map generated with the system illustrated in FIG. 1.
FIG. 3B illustrates a perspective view of each of the cross-sectional images of the image stack reviewed to generate the feature map illustrated in FIG. 3A.

The planning tool 102 can receive data from the OCT device 118. The data can include one or more A-scans, B-scans, and/or en face images. In some implementations, the planning tool 102 can generate the B-scans and the en face images from the A-scans received from the OCT device 118. The planning tool 102 stores the received (or generated) data in the storage element 108. The plurality of B-scans can be stored in the cross-sectional image database 110. The en face database 112 can store one or more en face images that correspond to the B-scans in the cross-sectional image database 110. For example, the B-scans stored in the cross-sectional image database 110 can represent cross-sectional views of at least a portion of an en face image stored within the en face database 112. The relationship between each of the cross-sectional images of the cross-sectional image database 110 and the en face images stored in the en face database 112 are stored in the coordinates database 114. For example, and as described further in relation to FIG. 3, one or more coordinates can relate each of the cross-sectional images to an en face image.

The planning tool 102 includes a mapping engine 104. In some implementations, the mapping engine 104 is configured to include a review mode and a surgical mapping mode. In the review mode, prior to surgery, a patient's eye is scanned with the OCT device 118 to generate a plurality of cross-sectional images of the surgery area. The cross-sectional images are stored in the cross-sectional image database 110, and the planning tool 102 displays each of the cross-sectional images onto the display 120 to enable a medical provider to review each of the cross-sectional images for features of interest. If a cross-sectional image includes a feature of interest, then the medical provider can flag the cross-sectional image with the input device 122. In some implementations, the features of interest are structural features of the eye such as the Schlemm's canal, the Collector channel, trabecular meshwork, aqueous vascular structures, outflow vessel densities, and a drainage angle of internal landmarks. In some implementations, the features of interest can also include functional and mechanical information about the eye.

Functional features of interest can provide information about the mechanical and functional aspects of the eye. The functional information can include fluid flow rates and volumes of the outflow pathway of the eye. The functional information can also include information from tests, such as acute intraocular pressure (IOP) elevation test, which can provide information about the trabecular meshwork's stiffness.

When the cross-sectional image is flagged by the user, a bit of an array can be set within the FOI database 116. For example, the FOI database 116 may initially include an array the length of the number of images stored in the cross-sectional image database 110. Each of the bits of the array can be initially set to 0. Setting the bit when a feature of interest is found can include setting the bit that corresponds to the cross-sectional image to 1, indicating that the flagged cross-sectional image includes a feature of interest. In another example, flagged cross-sectional images can be copied or moved to the FOI database 116, and in another example each of the cross-sectional images can have a unique identifier that is copied to an array within the FOI database 116 when the medical provider determines that the cross-sectional image includes a feature of interest.

In some implementations, when reviewing the cross-sectional images the medical provider can select a specific region within the cross-sectional image that includes the feature of interest. In these implementations, the coordinates of the feature of interest within the cross-sectional image can also be saved within the FOI database 116. In some implementations, the coordinates saved to the FOI database 116 relate to the x-y coordinates of the pixels of the area selected by the medical provider as including the feature of interest. For example, the upper, left pixel of the cross-sectional image may have the coordinates of (0,0), and the lower, right pixel (x, y), where x is the width of the image and y is the height of the image. The medical provider may draw a box (or other shape) around the feature of interest and the coordinates of the box on the x-y axis of the image can be saved to the feature of interest database 116 with an indication from which cross-sectional image the feature of interest is located. When the mapping engine 104 is in the surgical mapping mode, as further described in relation to FIG. 3, the mapping engine 104 maps the coordinates stored in the FOI database 116 onto the en face image to create point feature maps.

Still referring to FIG. 1, the system 100 can also include an outflow pathway visualizer 120. The outflow pathway visualizer 120 includes one or more instructions, applications, scripts, or libraries that are executed by the processor 106. The outflow pathway visualizer 120 is configured to enable non-invasive visualization of the aqueous humor outflow pathway in a living eye. The outflow pathway visualizer 120 is configured to analyze data received from the OCT device 118. In some implementations, the outflow pathway visualizer 120 processes the OCT data using different algorithms to generate different images. The outflow pathway visualizer 120 can then combine each of the different generated images to produce a composite image that reveals features not visible by a single technique. For example, standard OCT image processing techniques may not be well suited to capture relatively large blood vessels because the reflectivity of the blood in the blood vessels causes the blood vessels to disappear in the image.

In some implementations, the outflow pathway visualizer 120 is configured to analyze the OCT data from the OCT device 118 with split-spectrum amplitude decorrelation algorithm (SSADA)—yielding a SSADA-derived image. The SSADA generates an image that includes the moving, back-scattering media, which includes the blood within blood vessels. In general, the SSADA works by receiving data from the OCT device 118. The data includes a plurality of B-scans, each of which include a plurality of A-scans. The outflow pathway visualizer 120 then splits the spectrum of the plurality of B-scans into different frequency bands. In some implementations, the bandpass filters used to split the spectrum overlap no frequency components contained in the original data are lost. After slitting the B-scans, a decorrelation image is generated by calculating a decorrelation value between each of the adjacent B-scans (e.g., B-scanN and B-scanN+1, B-scanN+1 and B-scanN+2, etc). By splitting the full OCT spectrum into bands, the resulting image is made isotropic and less susceptible to axial motion noise. Flow through the limbus is typically within the transverse direction. Movement of blood in the transverse direction is captured and displayed by the SSADA-derived image. Because the blood flow occurs through blood vessels, the SSADA-derived image illustrates the blood-containing vasculature within the limbus. The mapping engine 104 of planning tool 102 can map the composite images generated by the outflow pathway visualizer 120 to the en face images to create structural feature maps of the outflow pathway.

In some implementations, the planning tool 102 interfaces with additional databases or testing apparatus to receive data relevant to the features of interest. For example, when the feature of interest includes mechanical or functional information, the planning tool 102 can interface with a database to receive the mechanical or functional information. In one example, a IOP elevation test may be performed on the patient prior to surgery. The IOP elevation test results can indicate the trabecular meshwork's stiffness. The IOP elevation test can be performed by imaging the eye with an OCT device while an ophthalmodynamometer applies force to the eye. The OCT image captured during the IOP elevation test can be saved to a database and then retrieved by the planning tool 102. The planning tool can analyze the OCT image for Schlemm's canal collapse, which can indicate softer regions of the trabecular meshwork by comparing the OCT image to a baseline OCT image when no pressure was applied to the eye. In some implementations, functional features of interest are measured by functional imaging of the eye. For example, a fluorescein canalogram can be performed to visualize both the episcleral veins and the intrascleral veins of the eye. During the fluorescein canalogram, using a cobalt blue filter, fluorescein tracers can be visualized as the tracer flows through the Schlemm's canal and into its tributaries and distal outflow vessels. The density of the tracer-filled vessels is then quantified. The density is quantified by dividing the video images of the tracers flowing through the vessels into four quadrants and processing the video images to remove the blue and red color channels. The images are then converted to stacked frames in an 8-bit video format. The vessels distal to Schlemm's canal are optimized for brightness and contrast while maintaining the constrain aspect ratio. The density of the tracer-filled vessels is determined in each quadrant in three non-over lapping fixed areas in each quadrant. The diameters of the tracer-filled vessels are measured four times relative to the catheter diameter, and the average diameter is determined.

The system 100 can also include a display 120 for displaying the cross-sectional images, en face images, and feature maps to a user of the system 100. The display 120 can be any type of computer or other monitor. The display 120 may be color or black and white. Example displays 120 can include, but are not limited to, liquid crystal displays (LCDs) and active-matrix organic light-emitting diode (AMOLED) displays. In some implementations, the display 120 may by connected to the planning tool 102 over a network. For example, the feature maps may be provided to a user's tablet computer or other hand held device for display over a network. In some implementations, the system 100 can include a plurality of displays 120. For example, the planning tool 102 may be on a central server that is linked to a plurality of workstations. A surgeon may review the cross-sectional images pre-operatively on a first screen, and then display the feature map on a second screen within the surgery suite during the surgery. As described above, the system 100 can include an input device 122 that is used for the selection of features of interest. The input device 122 can be a mouse, keyboard, or in some implementations, the display 120 includes a touch sensitive display.

The storage element 108 of the system 100 may include one or more hard disk drives or redundant arrays of independent disks for storing images, processor executable instructions, and other data. The example storage element 108 can include one or more hard disk drives (HDD); one or more optical drives including CD drives, DVD drives, or BLU-RAY drives; one or more solid-state drives (SSD); one or more USB flash drives; or any other device suitable for storing data. In some implementations, the storage element 108 may be non-volatile, mutable, or read-only. In some implementations, the storage element 108 may be connected to the other components of the system 100 via a network (e.g., a local area network, the internet, a cellular network, or a wide area network).

Figure 2:
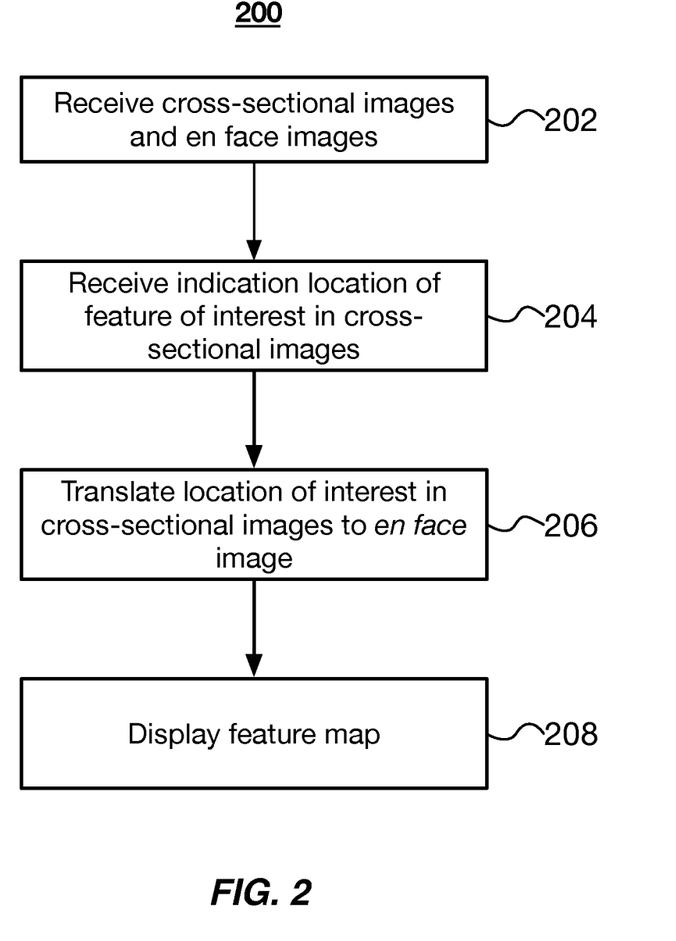
FIG. 2 illustrates an example method for generating a feature map using the system illustrated in FIG. 1.

FIG. 2 illustrates an example method 200 for generating a feature map. The method 200 includes receiving cross-sectional images and en face images (step 202). The method 200 also includes receiving an indication of a feature of interest location (step 204). The method 200 can include translating the location of the feature of interest in the cross-sectional images to the en face image (step 206). Finally, the feature map is displayed to the user (step 208).

As set forth above, the method 200 includes receiving cross-sectional images and en face images (step 202). In some implementations, an OCT device provides the cross-sectional images and the en face images to a planning tool. In other implementations, the planning tool is provided A-scans from the OCT device and constructs the cross-sectional images and en face images from the A-scan data. The cross-sectional images can include features of interest that a surgeon may want to target or avoid during a surgery. In some implementations, the received cross-sectional images are referred to as an image stack.

The method can also include receiving an indication of a location of a feature of interest in the cross-sectional image (step 204). In some implementations, after the generation or receipt of the cross-sectional images, the cross-sectional images are displayed to a user, such as a medical professional. The planning tool can display the images to the medical professional when the planning tool is in the reviewing mode. The user may review one or more of the cross-sectional images to determine which, if any, of the cross-sectional images include features of interest. Using an input device, the user may flag any cross-sectional image that includes a feature of interest. In some implementations, after determining that a cross-sectional image includes a feature of interest a user can further refine the selection of the feature of interest by drawing a box around the feature of interest within the image. The mapping engine can save the coordinates of the feature of interest to the coordinates database 114. The coordinates can indicate where in the image stack the cross-sectional image with the feature of interest is located and also the coordinates for where in the selected cross-sectional image the feature of interest resides.

The method can also include retrieving structural and functional information from a storage element. The structural information can include vascular and outflow pathway structures, and the functional information can include pathway flow rates and volumes and trabecular meshwork stiffness.

The location of the features of interest in the cross-sectional images are then translated to the en face image (step 206). The generation of the feature map by translating the selected features to the en face images can occur when the planning tool is in the surgical mapping mode. When the planning tool is placed into the surgical mapping mode, the mapping engine can retrieve the coordinates of the identified features of interest and translate the location of the features of interest from the coordinate system of the cross-sectional images to the coordinate system of the en face image. The plurality of cross-sectional images are cross sections of the en face image, and accordingly have specific locations and coordinates within the en face image. For example, the stack of cross-sectional images can be from a known portion (e.g., a rectangular portion) of the en face image. The location of the known portion can be represented by one or more bounding points (e.g., the corners of the rectangle). The coordinates stored in the coordinate database indicate where in the image stack the features of interest reside. The mapping engine then translates the location of the features of interest in the image stack to the en face image.

Once the features of interest are translated to the en face image, the feature map is displayed (step 208). As described further in relation to FIG. 3, a feature map is overlaid on the en face image to indicate the location of the selected features of interest. In some implementations, the markers can facilitate longitudinal comparisons of images. In some implementations, additional information such as the depth of the feature and the type of feature is also displayed on the feature map. The feature map can also display the cross-sectional images that were selected during the review mode that include the features of interest. In some implementations, the feature map can include functional and biomechanical information in addition to structural information. For example, a mask of the outflow vessel densities can be superimposed on the en face image to form a feature map that includes both features of interest identified by the surgeon and vessel densities.

FIG. 3A illustrates an example feature map 300 generated by the planning tool. The feature map 300 is a point feature map and includes an en face image 302 and a plurality of feature containing cross-sectional images 304(1)-304(N) (cumulatively referred to as feature containing cross-sectional images 304), where N is the total number of feature containing cross-sectional images selected by a medical professional. The feature containing cross-sectional images 304 are selected by a user from a stack of cross-sectional images that include Y cross-sectional images. The stack of cross-sectional images covers the area of the en face image defined by the box 306.

The stack of cross-sectional images is conceptually illustrated by FIG. 3B. FIG. 3B illustrates a perspective view of each of the cross-sectional images 308 of the stack of cross-sectional images within a three-dimensional box 306' (the three dimensional counterpart to box 306). The stack includes cross-sectional images 308(1)-308(Y), which are arranged in order within the box 306', which has a three-dimensional coordinate system. The en face image can be generated by integrating up along the z-axis of each of the cross-sectional images.

As described above, a user can scan through each of the cross-sectional images 308 to identify features of interest. A user can then flag a cross-sectional image 308 as including a feature of interest, and the planning tool can translate the x, y, z coordinate system of the cross-sectional images 308 in box 306' to the x and y coordinate system of the box 306 that overlays the en face image 302. For example, flagging a cross-sectional image 308 as including a feature of interest can provide the x coordinate along the box 306 of the feature in the en face image 302. Continuing this example, and as illustrated in FIG. 3B, if a user indicates that the 7th cross-sectional image includes a feature of interest, the x coordinate for the feature is x=7. If the user further defines the feature of interest, by drawing a box around the feature of interest, the box can provide the y coordinate for the feature. For example, in cross-sectional image 308(7), which in FIG. 3B is shifted out of the stack, if the box 310 made by the user spans from (110, 240) in the upper left to (340, 425) in the lower right of cross-sectional image 308(7), the feature of interest would span from (73, 110) to (73, 340) in box 306. In some implementations, the depth of the feature of interest is provided by the y coordinate value form the user defined selection box 310. For the purpose of this example, assuming that the feature indicated by box 310 is the first feature identified in the stack, the area of the cross-sectional image defined by the box 310 is the feature containing cross-sectional images 304(1). The location of the feature is then indicated to the medical professional by a marker 312 in the point feature map. A point feature map can include one or more markers 312 that indicate the location on features identified in the cross-sectional images 308 on the en face image 302.

Figure 4:
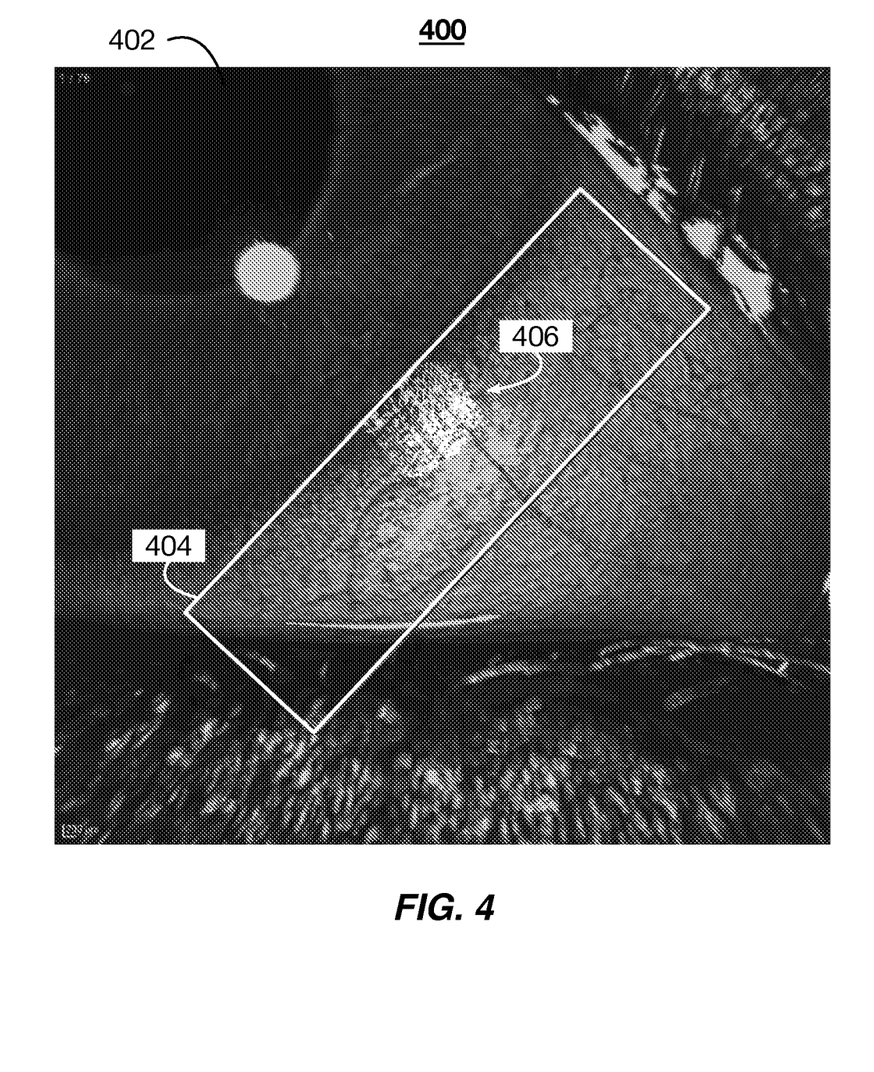
FIG. 4 illustrates another example feature map generated with the system illustrated in FIG. 1.

FIG. 4 illustrates another example feature map 400 generated with the planning tool described herein. The feature map 400 includes an en face image 402. In some implementations, the feature map 400 can also include a plurality of feature containing cross-sectional images, as illustrated in relation to feature map 300. The stack of cross-sectional images cover the area of the en face image defined by the box 404. FIG. 4 illustrates that in some implementations, the feature maps generated by the planning tool can also include biomarkers that are illustrated as structures that are superimposed on the en face image. For example, feature map 400 includes a superimposed image 406 that illustrates the location and structure of the aqueous vascular structure. In some implementations, the vascular structure is referred to as a tree map or a vascular casting and provides the surgeon with an indication of the location of the vascular structure of the eye. In some implementations, images of other internal structures can be superimposed on the en face image.

Figure 5:
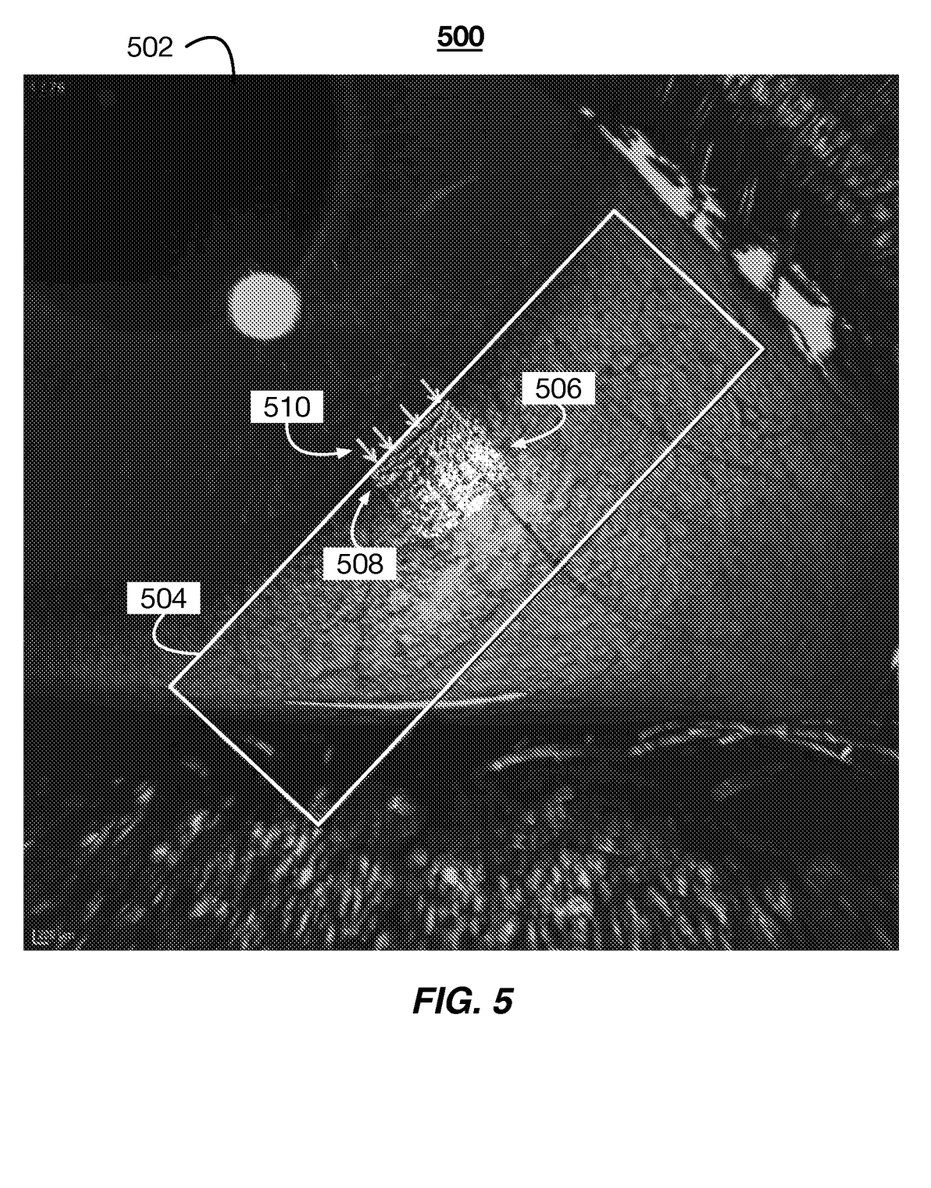
FIG. 5 illustrates another example feature map generated with the system illustrated in FIG. 1.

FIG. 5 illustrates another example feature map 500 generated with the planning tool described herein. The feature map 500 includes an en face image 502. In some implementations, the feature map 400 can also include a plurality of feature containing cross-sectional images, as illustrated in relation to feature map 300. The stack of cross-sectional images cover the area of the en face image defined by the box 504. In addition to the superimposed image 506 that illustrates structural features of the eye (e.g., the vascular structure of the eye as discussed above in relation to FIG. 4), the feature map 500 includes a second superimposed image 508. The second superimposed image 508 illustrates functional information about the eye. The functional information can include fluid flow and other biomechanical information about the eye. The combination of the superimposed images 506 and 508 can provide a medical professional with information about the structure and the function of the eye. In some implementations, the second superimposed image 508 of the functional features of interest is color coded to indicate a level of function. For example, in the superimposed image 508 the red regions (indicated by the arrows 510) indicate the areas of greatest collapse and the green regions indicate the areas of the least amount of collapse during an IOP elevation test. In some implementations, the feature maps described herein can include point feature maps, structure feature maps, functional feature maps, or any combination thereof.

Figure 6:
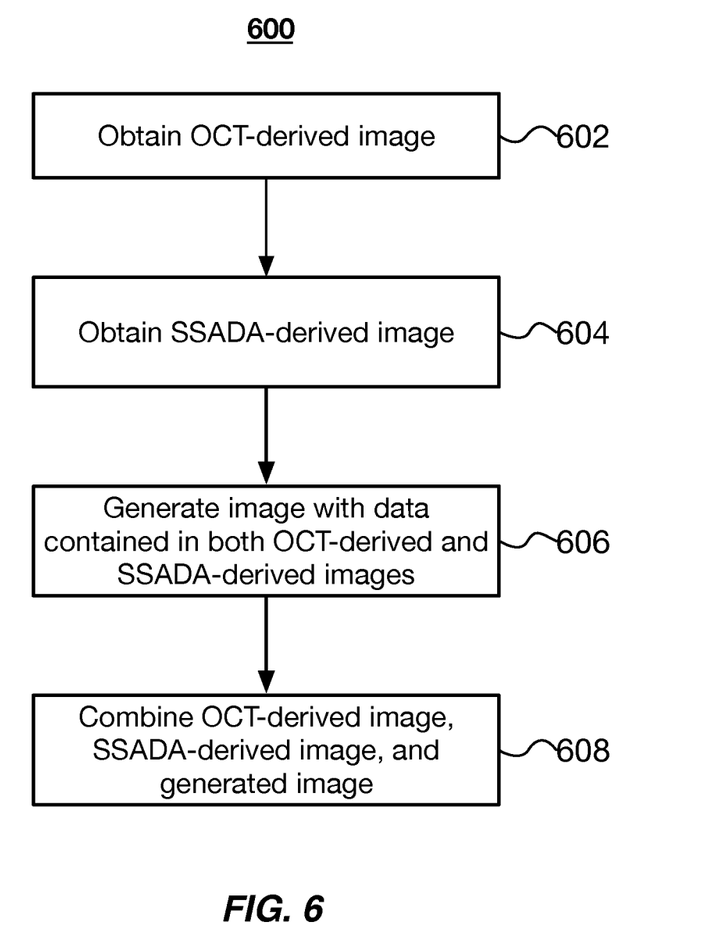
FIG. 6 illustrates a flow chart of an example method for mapping the aqueous humor outflow system.

FIG. 6 illustrates a flow chart of an example method 600 for mapping the aqueous humor outflow system. The method 600 includes obtaining an OCT-derived image (step 602) and a SSADA-derived image (step 604). From the OCT-derived image and the SSADA-derived image, a third image is generated from the data contained within both the OCT-derived image and the SSADA-derived image (step 606). The method 600 also includes combining the OCT-derived image, the SSADA-derived image, and the third image to form a composite image (step 608).

Figure 7:
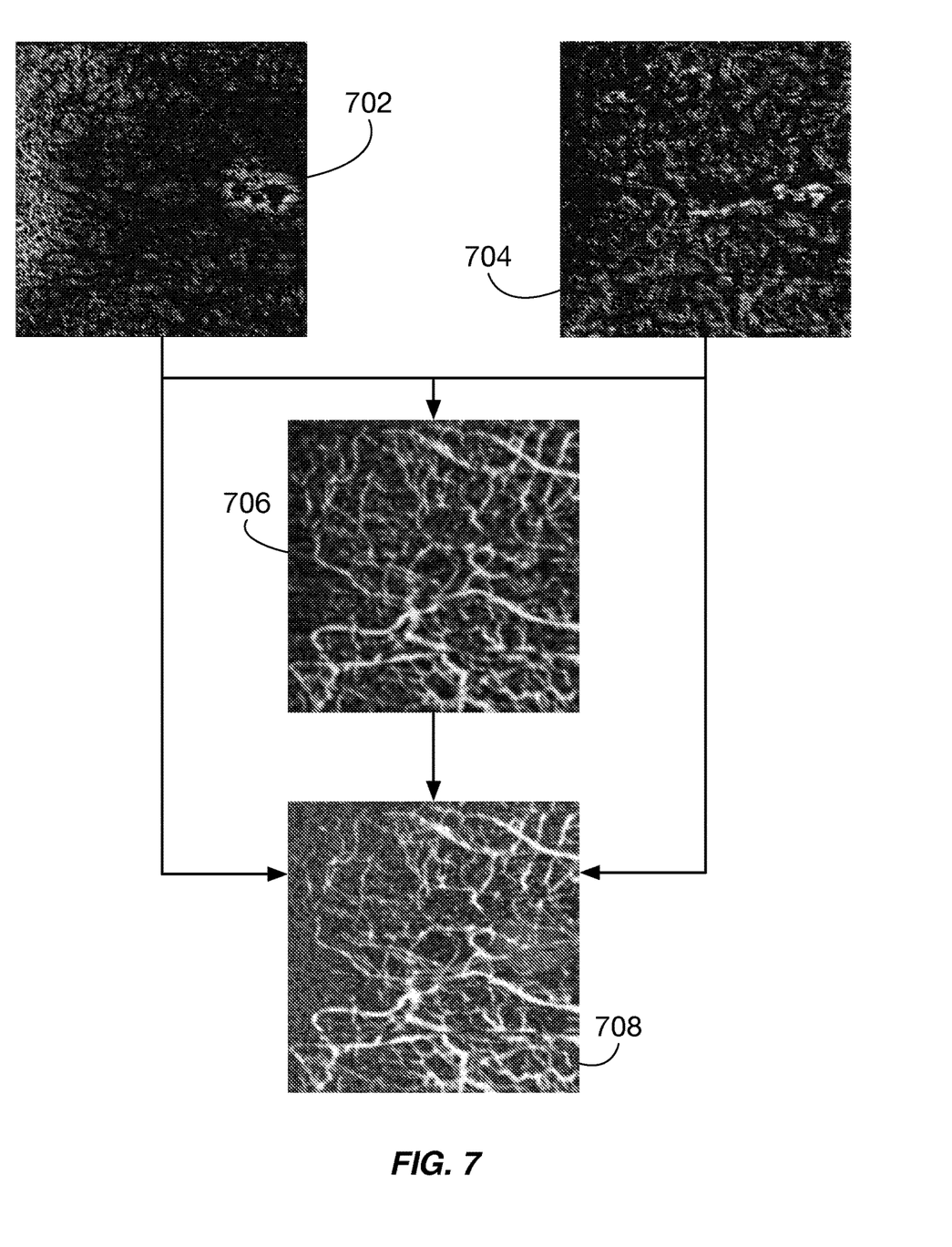
FIG. 7 illustrates an example image during the various steps of the method illustrated in FIG. 6.

As set forth above, and also referring to FIG. 7, the method 600 includes obtaining an OCT-derived image (step 602) and a SSADA-derived image (step 604). Image 702, illustrated in FIG. 7, illustrates an example OCT-derived image. Once the OCT data is received from the OCT device, the system described herein can further process the OCT data with a SSADA to generate a SSADA-derived image 704. In some implementations, the OCT-derived image illustrates the vasculature within the limbus used to transport aqueous humor. The vessels can include the small vessels adjacent to, and including, the Schlemm canal. The SSADA-derived image illustrates the vasculature within the limbus used to transport blood. The vasculature illustrated by the SSADA-derived image can relatively larger blood vessels.

The method 600 can also include generating a third image (step 606). In some implementations, the third image illustrates the transition between aqueous humor containing vasculature and the blood containing vasculature. In some implementations, the third image is generated by combining the OCT-derived image and the SSADA-derived image with a logical AND. Image 706 illustrates the logical combination of image 702 and image 704 with a logical AND. The process of combining the OCT-derived image and the SSADA-derived image with a logical AND generates an image that illustrates the features that are common to both the OCT-derived image and the SSADA-derived image. In some implementations, the amount of common features to both the OCT-derived image and the SSADA-derived image can be controlled by varying the intensity of the signal used to capture the OCT data. For example, a higher signal intensity may enable to the SSADA-derived image to capture images with only a small amount of blood and a relatively high concentration of aqueous humor, which results in more features common to both the OCT-derived image and the SSADA-derived image.

At step 608, the method 600 includes combing the OCT-derived image, the SSADA-derived image, and the third image. Image 708 of FIG. 7 illustrates a composite image of image 702, image 704, and image 706 using method 600. In some implementations, one or more of the images are pseudo-colored prior to the combination process. For example, and as illustrated in FIG. 7, the OCT-derived image is colored on a blue-black scale, the SSADA-derived image is colored on a red-black scale, and the third image is colored on a white-black scale. Accordingly, in image 708, the blue colored vessels include predominately aqueous humor, the red colored vessels include predominately blood, and the white colored vessels include a mix of blood and aqueous humor.

In some implementations, at least a portion of the image generated using method 600 is used in the above described method 200 of generating a feature map. The image generated using method 600 can be used in addition to, or in place of, the images and features described above in relation to method 200. For example, and also referring to FIG. 4, the superimposed image 406 may be generated using the image generated using method 600.

COMPUTER APPARATUS AND PROCESSING

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, an intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

DEFINITIONS

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the U.S. Patent Office Manual of Patent Examining Procedures, Section 2111.03

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. All publicly available documents referenced herein, including but not limited to U.S. patents, are specifically incorporated by reference.

The invention claimed is:

1. A surgical mapping tool comprising:
   (a) one or more data processors; and
   (b) one or more storage devices storing instructions that when executed by the one or more data processors cause the one or more data processors to:
   (i) retrieve, from the one or more storage devices, image data from an optical coherence tomography device;
   (ii) receive an indication of a location within a first coordinate system of a feature of interest within the received image data;
   (iii) translate the indication of the location to a location within a second coordinate system on an en face image; and
   (iv) display a marker on the en face image at the location within the second coordinate system on the en face image.

2. The surgical mapping tool of claim 1, wherein the image data includes at least one of each of an A-scan, a B-scan, and an en face image.

3. The surgical mapping tool of claim 1, wherein the image data includes a plurality of A-scans.

4. The surgical mapping tool of claim 3, wherein executing the instructions by the one or more data processors causes the one or more data processors to generate: (a) a plurality of B-scans; and (b) at least one en face image from the plurality of A-scans.

5. The surgical mapping tool of claim 1, wherein the feature of interest is at least one of a structural feature of interest and a functional feature of interest.

6. The surgical mapping tool of claim 5, wherein the structural feature of interest is at least one of a Schlemm's canal, a Collector channel, and a trabecular meshwork.

7. The surgical mapping tool of claim 5, wherein the functional feature of interest is at least one of an outflow vessel density, a fluid flow rate, a fluid flow volume, or a stiffness of a trabecular meshwork.

8. The surgical mapping tool of claim 5, wherein the marker comprises a feature map of the feature of interest overlaid on the en face image.

9. The surgical mapping tool of claim 1, wherein the indication of the location of the feature of interest identifies the feature of interest within a cross-sectional image.

10. The surgical mapping tool of claim 1, wherein execution of the instructions by the one or more data processors causes the one or more data processors to:
    (a) obtain a split-spectrum amplitude decorrelation algorithm (SSADA)-derived image,
    (b) generate a third image by logically combining the SSADA-derived image and the image data from the optical coherence tomography device; and
    (c) combine each of the third image, the image data from the optical coherence tomography device, and the SSADA-derived image to produce a hybrid image.

11. The surgical mapping tool of claim 10, wherein the feature of interest comprises the hybrid image.

12. A method of identifying features of interest, the method comprising:
    retrieving, by a planning tool from a storage device, image data from an optical coherence tomography device;
    receiving, by the planning tool, an indication of a location within a first coordinate system of a feature of interest within the received image data;
    translating, by the planning tool, the indication of the location to a location within a second coordinate system on an en face image; and
    displaying, by the planning tool, a marker on the en face image at the location within the second coordinate system on the en face image.

13. The method of claim 12, wherein the image data includes at least one of each of an A-scan, a B-scan, and an en face image.

14. The method of claim 12, wherein the image data includes a plurality of A- scans.

15. The method of claim 14, further comprising generating a plurality of B-scans and at least one en face image from the plurality of A-scans.

16. The method of claim 12, wherein the feature of interest is at least one of a structural feature of interest and a functional feature of interest.

17. The method of claim 16, wherein the structural feature of interest is at least one of a Schlemm's canal, a Collector channel, and a trabecular meshwork.

18. The method of claim 16, wherein the functional feature of interest is at least one of an outflow vessel density, a fluid flow rate, a fluid flow volume, or a stiffness of a trabecular meshwork.

19. The method of claim 16, wherein the marker comprises a feature map of the feature of interest overlaid on the en face image.

20. The method of claim 12, further comprising:(a) obtaining a split-spectrum amplitude decorrelation algorithm (SSADA)-derived image; (b) generating a third image by logically combining the SSADA-derived image and the image data from the optical coherence tomography device; and (c) combining each of the third image, the image data from the optical coherence tomography device, and the SSADA-derived image to produce a hybrid image.

* * * * *